United States Patent [19]

Yuspa et al.

[11] Patent Number: 5,302,511

[45] Date of Patent: * Apr. 12, 1994

[54] ANTIBODIES TO PEPTIDES UNIQUE TO SPECIFIC KERATIN PROTEINS

[75] Inventors: Stuart H. Yuspa, Bethesda; Dennis R. Roop, Garrett Park; Peter Steinert, Rockville, all of Md.

[73] Assignee: The United States of America as represented by the Department of Health and Human Services, Washington, D.C.

[*] Notice: The portion of the term of this patent subsequent to Feb. 2, 2005 has been disclaimed.

[21] Appl. No.: 571,513

[22] Filed: Aug. 14, 1990

Related U.S. Application Data

[63] Continuation of Ser. No. 110,305, Oct. 20, 1987, abandoned, which is a continuation-in-part of Ser. No. 654,213, Sep. 25, 1984, Pat. No. 4,722,895.

[51] Int. Cl.[5] .................... A61K 35/14; C07K 3/00; C07K 13/00; C07K 15/00
[52] U.S. Cl. .................... 435/7.21; 530/389.2; 530/389.3; 530/388.1; 530/388.85; 530/357; 435/7.2; 435/7.23; 435/7.92; 435/7.93; 435/7.94; 435/7.95; 436/501; 436/503; 436/519

[58] Field of Search .................. 435/7.21, 172.3, 7.2, 435/7.23, 7.92, 7.93, 7.94, 7.95; 530/357, 387, 389.2, 389.3, 388.1, 388.85; 935/81; 436/501, 503, 519

[56] References Cited

U.S. PATENT DOCUMENTS 4,366,246 12/1982 Riggs et al. ............................ 435/68
4,722,895 2/1988 Yuspa et al. ........................... 435/68

OTHER PUBLICATIONS

Roop et al. Proc. Natl. Acad. Sci. (USA) 80:716–720, 1983.
Steinert et al. Nature 302: 794–800, 1983.

Primary Examiner—Christine M. Nucker
Assistant Examiner—David R. Preston
Attorney, Agent, or Firm—Birch, Stewart, Kolasch & Birch

[57] ABSTRACT

By cloning the gene for particular keratin proteins, it has been possible to determine amino acid sequences of specific keratins. This has made possible selection of sequences which are unique to a given keratin. The production of antibodies that respond to selected sequences provides means of selectively identifying specific keratins. These diagnostic tools provide means of identifying cell source of malignancies.

13 Claims, 4 Drawing Sheets

| | | | | | | | | | | | | |
|---|---|---|---|---|---|---|---|---|---|---|---|---|
| 67 kd | T | V | K | F | V | S | T | S | Y | S | R | G | T | K-COOH |
| 59 kd | T | S | G | G | G | D | Q | S | S | K | G | P | R | Y-COOH |
| 60 kd | K | Y | T | T | T | S | S | S | K | K | S | Y | R | Q-COOH |
| 55 kd | K | V | V | S | T | H | E | Q | V | L | R | T | K | N-COOH |

```
  1  SVRYSSSSKQ FSSSRSGGGG GGGSSLRISS SKGSLGGGFS SGGFSGGGSFS RGSSGGGCFG
 61  GSSGGYGGLG GFGGGSFRGS YGSSSFGGSY GGSFGGGSFG GGSFGGGSFG GGGFGGGGFG
121  GGFGGGFGGD GGLLSGNEKV TMQNLNDRLA SYLOKVRALE ESNYELEGKI KERYDOHGNS
181  ROGEPRDYSK YYKTIDDLKN QILNLTTDNA NILLOIDNAR LAADDFRLKY ENEVALRQSV
241  EADINGLRRV LDELTLTQAD LEMQIESLTE ELAYLKKNRE EEMKHLRNVS TGDVNVEMNA
301  APGVDLTQLL NNMRNQYEQL AEQNRKDAEA WFNEKSKELT TEIDNNIEQI SSYKSEITEL
361  RRNVQALEIE LQSQLALKQS LEASLAETEG RYCVQLSQIQ AQISALEEQL QEIRAETECQ
421  NTEYQQLTDI KIRLENEIQT YRSLLEGEGS SGGGGRGGGS FGGGYGGGSS GGGSSGGGYG
481  GGSSSGGHGG SSSGGYGGGS SGGGGGGYGG GSSGGSSSG GGYGGGSSSG GGY_GGSSSG
541  GHKSSSSGSV GESSSKGPRY
```

FIG. 4

```
Mouse SCGGGYSGGG GGSSCGGGYS GGGGGSSCGG GSYSGGGSGC GGGGGSGGGG GGSGGGGGGG
Mouse SSCGGGSSGG GGGGSSCGGG SSGGGSSCGG SGGGGYSGGG GGSCGGGYSG GGGSSGGSSC
Mouse GGGYSGGGGG SSCGGGGGSS GGGSSGGGSS GGGGGGSSQQ YQCQSYGGGS SGGSSCGGGY
Mouse SGGGGSSCGG GSSGGGGSCG GSGGGGYSGG GGGSCGGGSS GGGGGYSSQ  RTRQTSCAPQ
Mouse QSYGGGSSGG GGSCGGGSSG GGGGGSYSS  GGGGSSGGCG GGYSGGGGGC GGGSGGGRGG
Mouse GCGGGSSCGG GGGCGGGYSG GGGGGSSCGG GSSGGGSGGG KGVPVCHQTQ QKQAPTWPCK
Human ......SGSG CIISGGGSVC GGSVGGGGGG GSSVGGGGSG KGVPVCHPAQ QKQAPTW....
```

ANTIBODIES TO PEPTIDES UNIQUE TO SPECIFIC KERATIN PROTEINS

This application is a continuation of application Ser. No. 07/110,305, filed Oct. 20, 1987, now abandoned, which is a continuation-in-part of U.S. Ser. No. 06/654,213 filed Sep. 25, 1984, now U.S. Pat. No. 4,722,895.

BACKGROUND

Human cells contain a proteinaceous structural framework called a cytoskeleton. Each cell type contains a different protein or proteins as its cytoskeleton. For example, a brain cell's cytoskeleton is different than a muscle cell's or a lung cell's. In short, one means of differentiating cells is through an analysis of the proteins of the cytoskeleton.

Such differentiation, however, was only a theoretical concept due to impossibility of differentiating epithelial cells. Epithelial cells form the epidermis and line hollow organs and all passages of the respiratory, digestive, and genito-urinary systems. These are the host common cells of the human body. Therein, however, lies the problem. It was discovered that epithelial cells could be differentiated from the other major cell types (mesenchymal, glial, neuronal, and muscle cells) by the presence of keratin proteins in the cytoskeleton.

The intermediate filaments found in keratinocytes and other epithelial cells are composed of about 20 different keratin subunits. Each of these 20 proteins differ by as little as 10–12 amino acid sequences. The subunits expressed in a given epithelial cell vary widely depending on cell type, period of embryonic development, degree of differentiation, and growth environment of the cell. Changes in the pattern of keratin synthesis have also been observed during experimental skin carcinogenesis in established cell lines of malignant keratinocytes and in a variety of pathologic processes in the skin. Development of antisera specific to any one keratin subunit is, therefore, very useful for studies concerning expression and function of individual keratin proteins. This has proved difficult, however, since both polyclonal antibodies prepared against purified keratin subunits and monoclonal antibodies recognize more than one subunit. This shows that these antibodies are elicited against structural features common among keratin subunits. It is this similarity between the various keratin proteins that has made differentiation between epithelial cells most difficult.

The first tests developed to differentiate between epithelial cells involve monoclonal antibodies. These antibodies differentiate epithelial cells from non-epithelial cells, but they exhibit only limited utility in differentiating between epithelial cells. Monoclonal antibodies have been developed that are specific for groups of keratin proteins.

The difficulty in developing highly specific monoclonal antibodies or a differentiating reagent lies in the inability to determine the exact amino acid sequence of the protein. Antibodies developed prior to this invention are specific for amino acid sequences of the keratin protein common to all of the keratins and are, therefore, not individually specific.

The present invention discloses a method for producing monospecific antibodies to the individual keratin proteins. The reagents of this invention, therefore, are useful as diagnostic and differentiation reagents. More importantly, perhaps, these antibodies are useful in detecting and identifying specific types of carcinomas, mesotheliomas, adenocarcinomas, and other forms of malignancies arising from keratin-containing cells. The antibodies of the invention are, therefore, useful in identifying the site of origin of malignancies.

The present invention was made possible by the discovery of two technical advances of the invention: (1) cloning the gene for the keratin protein; and (2) establishing the amino acid sequences from the cloned keratin gene. The combination of these discoveries led to the elucidation of the amino acid sequences for each keratin protein. In broad terms, the invention is the development of antibodies which specifically react with sequences peculiar to each keratin protein. Exemplified are the methods for producing antibodies specific for keratins of 55 kD, 59 kD, 60 kD, and 67 kD molecular weight.

UTILITY

The products of this invention are useful in the histodiagnosis and classification of tumors and for the identification of transformed cells.

DESCRIPTION OF THE FIGURES

FIG. 1 provides a delineation of the specific sequences at the carboxy terminus of mouse keratins. Amino acid sequences were deduced from the nucleotide sequence of CDNA clones. Regions of the 67 kD and 59 kD keratins selected for synthesis are underlined.

FIG. 2 is an immunoblot analysis of antisera. A cytoskeletal extract of newborn mouse epidermis was subjected to electrophoresis, transferred to nitrocellulose paper and reacted with various antisera. Lane 1 was stained directly with Coomassie Blue. Lanes 2–6 were reacted with the following antisera: Lane 2, a multivalent keratin antiserum (1/25,000 dilution); Lane 3, anti-59 kD keratin peptide (1/2,000 dilution); Lane 4, preimmune serum for the anti-59 kD keratin peptide (1/2,000 dilution); Lane 5, anti-67 kD keratin peptide (1/800 dilution); and Lane 6, sreimmune serum for the anti-67 kD keratin peptide (1/800 dilution).

FIG. 3 shows translation products of mouse epidermal POIY(A)+ RNA. POIY(A)+ RNA was extracted from newborn mouse epidermis and translated in an in vitro reticulocyte system containing [$^{35}$S]-methionine. The labeled proteins were separated electrophoretically in an 8.5% polyacrylamide/NaDodSO$_4$ gel and visualized by fluorography. Lane 1, translation products of mouse epidermal Poly(A)+ RNA. Lane 2, translation products immunoprecipitated with keratin antiserum. Lane 3, translation products that had been allowed to react with control serum. The 55-kDal band is distorted by unlabeled IgG in the immunoprecipitate. T indicates an mRNA-independent artifact of the translation system.

FIG. 4 delineates the sequence of human keratin 10, Locus=HK10(57 K), 560 amino acids, Definition=-Translation of HK10, Origin=Translated from base 8 to base 1691.

FIG. 5 compares the sequences of mouse and human cell envelop proteins.

GENERAL DESCRIPTION

Synthetic peptides corresponding to the carboxy terminal amino acid sequences Of mouse keratins were first used to produce antibodies which proved highly specific for subunits unique to each keratin protein.

cDNA libraries to mRNA isolated from both terminally differentiating murine epidermis and undifferentiated murine epidermal cells (basal cells) were prepared. The cloned gene to the 59 kD and 67 kD keratins expressed in the former and 55 and 60 kD keratins expressed in basal cells are sequenced to deduce their amino acid sequence.

Once the amino acid sequence of the gene was determined, the amino acid sequence of the keratin protein could be determined. After the protein was sequenced, synthetic peptides corresponding to the unique aming acid sequence (the carboxy terminal amino acid sequences) are produced. These peptides were then used as immunogens which elicit highly specific keratin antibodies.

At the present time antibodies have been produced in rabbits and guinea pigs as well as in mice. The antibodies produced in these species to human keratins have proved useful in diagnosis of human skin diseases. Furthermore, it has been shown that lose or gain in number of keratins expressed in cells is often indicative of a diseased state. The use of screening tests to determine all keratins produced may be used to identify preneoplastic cells.

SPECIFIC DISCLOSURE

A library of CDNA clones was prepared from poly(A)+ RNA of newborn mouse epidermis. An epidermis sample was placed in liquid nitrogen and ground in a mortar. RNA was isolated from the ground epidermis with guanidine.HCl and enriched for poly(A)+ RNA using the procedure described in Fuchs and Green, *Cell*, Vol. 17, pp 573-582 (1979). 150 ug of epidermal poly(A)+ RNA was obtained after the enrichment process and was separated by electrophoresis in a 1.5% agarose gel containing 10 mM methylmercuryhydroxide. The gel was sliced into 2-mm fractions and the RNA isolated as described by Fuchs and Green, above. This RNA was then used to construct a cDNA library.

Double-stranded CDNA was synthesized with reverse transcriptase from poly(A)+ RNA isolated, above, and the hairpin loop was cleaved with S1 nuclease. Approximately 16 dCMP residues were added to the 3' ends of the double-stranded CDNA with terminal transferase. The tailed CDNA was annealed with plasmid vector pBR322 that had been linearized by cleavage with PstI restriction endonuclease and tailed with an average of 14 DGMP residues per 3,' terminus. An aliquot of this mixture was used to transform *Escherichia coli* K-12 strain RRI. Transformants containing recombinant plasmids with keratin cDNA inserts were identified by colony hybridization with [$^{32}$p]cDNA complementary to partially purified keratin mRNAs.

Recombinant plasmids produced above are then shown by hybrid selection analysis to contain cDNA sequences complementary to the mRNA encoding the particular keratins. The first made were sequences encoding 55 kD, 59 kD, 60 kD, and 67 kD keratins as exemplified. In a similar manner, human keratin 10 (57 kD) and human filaggrin having a 20 kD repeating unit is available. (See FIG. 4)

Determination of the sequences of the clones proceded in the following manner: The appropriate fragments were subjected to 5' and 3' labelling on both strands using the Maxam and Gilbert procedures in *Meth. Enzym.*, Vol. 65, pp 499-560 (1980). The clone pK 276 (0.536 kbp) began just upstream from the first NciI site and pK 435 (1.802 kbp) began two bases upstream from a DdeI site. Both clones are used as examples and encode the 59 kD keratin. The 5'-terminal sequence was then derived following primer extension of a probe consisting of a DdeI-SacI fragment.

Once the nucleotide sequencing was completed, the amino acid sequence of the protein is deduced based on the codons elucidated by the nucleotide sequencing. The carboxy terminal amino acid sequences for some of the keratins is shown in FIG. 1.

Synthetic peptides were then synthesized corresponding to the sequences shown in FIG. 1. Decatripeptides and decadipeptides were synthesized by wellknown solid-phase methods and were purified by high performance liquid chromatography. See Meyers and Coy, *J. Peptide Int. Protein Res.*, Vol. 16, pp 248-253 (1980) for a review.

These synthetic peptides were then coupled to bovine serum albumin (following the procedure described in Walter et al, *PNAS*, Vol. 77, pp 5197-5200 (1980)) and used to immunize rabbits according to the following schedule:

(1) 500 ug of coupled peptide in complete Freund's adjuvant (1:1) subcutaneously on day 0, (2) 500 ug of coupled peptide in incomplete Freund's adjuvant (1:1) subcutaneously on day 21, (3) 500 ug of coupled peptide in incomplete Freund's adjuvant (1:1) subcutaneously on day 42.

Blood taken from these animals after 7 weeks was shown by ELISA analysis to contain highly specific antibodies corresponding to synthetic peptides for keratins of m.w. 55 kD, 59 kD, 60 kD, and 67 kD. The specificity of the antisera is determined by immunoblot analysis against a cytoskeletal extract of newborn mouse epidermis, which mainly consists of the 59 kD and 67 kD keratins (FIG. 2, lane 1).

A previously described multivalent keratin antiserum, which was prepared against a partially purified preparation of the 59 kD keratin subunit, reacts with both the 67 and 59 kD keratins as well as with minor polypeptides of 64 and 62 kD. Both antisera produced against synthetic peptides were highly specific for their corresponding keratin polypeptide (FIG. 2, lane 3 and 5). Weak activity against the 67 kD keratin is present in both preimmune sera (FIG. 2 lanes 4 and 6) and is also observed in the anti-59 kD keratin peptide antiserum (FIG. 2, lane 3).

Antibodies to keratin 10 (Sequence disclosed in FIG. 4) were produced in a similar manner and used to provide antibodies in both guinea pigs and rabbits. Antibodies to envelop proteins, keratin 6, keratin 14, keratin 16, and filaggrin have all been made by this method.

EXAMPLE 1

Cloning of Keratin cDNAs: Double stranded cDNA was synthesized with reverse transcriptase from Poly(A)+ RNA isolated from newborn mouse epidermis and the hairpin loop was cleaved with S1 nuclease. Approximately 16 DCMP residues were added to the 3' ends of the double-stranded CDNA with terminal transferase. The tailed CDNA was annealed with plasmid vector pBR322 that had been linearized by cleavage with PstI restriction endonuclease and tailed with an average of 14 DGMP residues per 3' terminus. An aliquot of this mixture was used to transform *Escherichia coli* K-12 strain RRI. Transformants containing recombinant plasmids with keratin CDNA inserts were identified by colony hybridization with [$^{32}$p]cDNA complementary to partially purified keratin mRNAs. Plasmid DNA was then prepared from positive recombinants.

EXAMPLE 2

Hybridization-Selection Assay: The identity of recombinants selected in the initial screening was confirmed by the hybrid-selection assay essentially as described by Cleveland et al, Cell, Vol. 20, pp 95-109 (1980). Plasmid DNAs were linearized with EcoRI and 10 ug was bound to (13-mm) nitrocellulose filters (Schleicher and Schuell, BA85). The filter-bound DNA was prehybridized for 2 hr at 41° C. in 50% (vol/vol) formamide (Fluka)/0.4 M NaCl/10 mM 1,4-piperazine-diethanesulfonic acid, pH 6.4/5 mM EDTA/250 ug of poly(A)+ per ml/250 ug of yeast tRNA per ml/0.2% NaDodSO$_4$. Hybridization was for 20 hr at 41° C. in the same buffer (150 ul per filter) containing 15 ug of epidermal poly(A)+ RNA. The filters were washed two times (5 min each) with 1×NaCl/Cit/0.1% NaDodSO$_4$ at room temperature [×NaCl/Cit is 0.15 M NaCl/0.015 M trisodium citrate (standard saline citrate)], three times (5 min each) with 0.1×NaCl/Cit/0.1% NaDodSO$_4$ at room temperature, and two times (5 min each) with 0.1×NaCl/Cit/0.1% NaDodSO$_4$ at 60° C. for filters containing pK335 and pK1005 DNA and at 68° C. for the filter containing pK276 DNA. RNA was eluted from the filters in 300 ul of water at 100° C. for 2 min. The RNA was collected by precipitation in the presence of 10 ug of yeast tRNA and analyzed by translation in the rabbit reticulocyte system.

EXAMPLE 3

Figure 3:
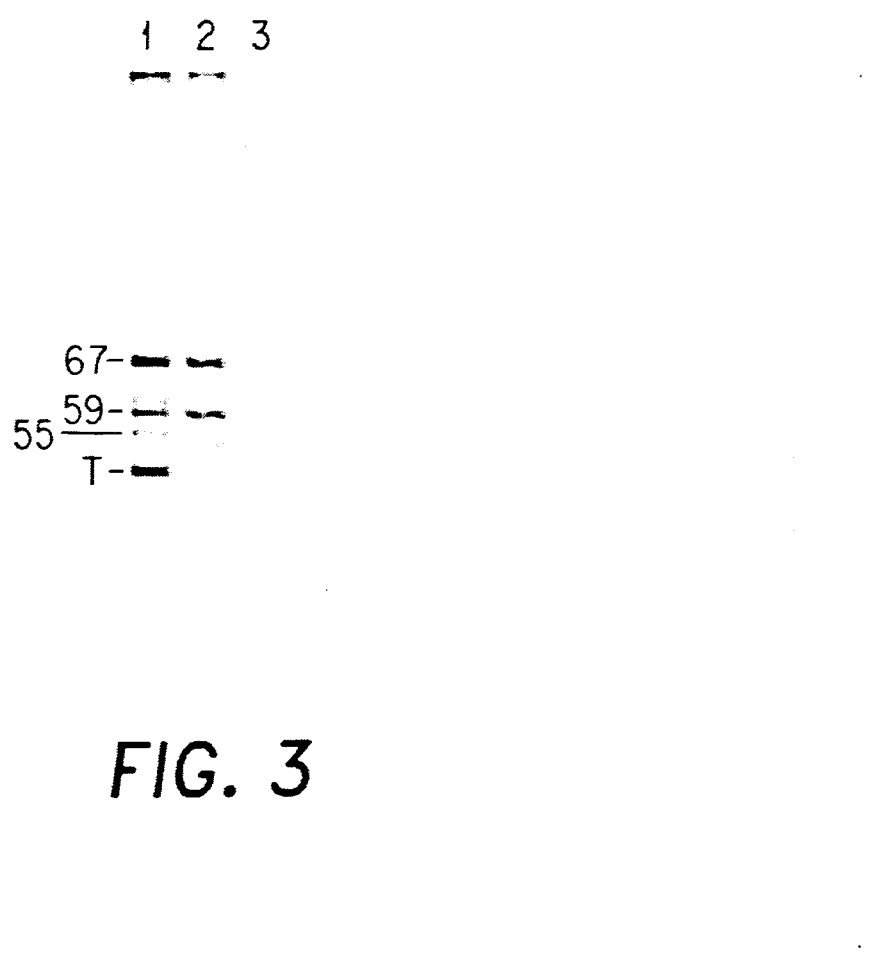

Cloning DNAs Complementary to keratin mRNAs: The translation products of total poly(A)+ RNA isolated from newborn mouse epidermis are shown in FIG. 3, lane 1. Immunoprecipitation of these products with antiserum prepared against keratins present in mouse stratum corneum demonstrated that the most abundant mRNAs present in this tissue code for keratins are 55, 59, and 67 kdal (FIG. 3, lane 2). Previous studies have shown that this multivalent rabbit antiserum is able to react with most, if not all, of the keratins synthesized in intact epidermis and cultured epidermal cells. The band below T in lane 1 is actin. Because the concentration of keratin mRNAs was quite high in mouse epidermis, a CDNA library was constructed with CDNA synthesized from total epidermal poly(A)+ RNA. Recombinant plasmids were screened with CDNA synthesized from partially purified MRNA coding for the 59- and 67-kDal keratins. These mRNAs were obtained by fractionating epidermal poly(A)+ RNA in a 1.5% agarose gel containing 10 mM methylmercury hydroxide. The gel was sliced into 2.0 mm fractions and the RNA was isolated from each slice. Fractions 11 and 14 were enriched in MRNA coding for the 67- and 59-kDal keratins and these were used for the synthesis of [$^{32}$p]cDNA. In the process of screening the CDNA library with these cDNAs recombinants that contained sequences complementary to the MRNA coding for the 55-kDal keratin were also isolated.

We claim:

1. An antibody which specifically binds to one and only one of the proteins selected from the group consisting of: murine kerating 6, murine keratin 14, murine keratin 16 and murine filaggrin.

2. A composition of matter comprising one or more antibodies according to claim 1.

3. An antibody which specifically binds to one and only one of the proteins selected from the group consisting of: murine keratin 6, murine keratin 14, murine keratin 16 and murine filaggrin.

4. An antibody which specifically binds to one and only one of the proteins selected from the group consisting of: keratin of molecular weight 67 kildaltons, keratin of molecular weight 60 kilodaltons, keratin of molecular weight 59 kilodaltons and keratin of molecular weight 55 kilodaltons.

5. An antibody according to claim 4, which specifically recognizes the peptide or a portion thereof defined by an amino acid sequence selected from the group consisting of: TVFVSTSYSRGTK, TSGGGDQSSKGPRY, KYTTTSSSKKSYRQ and KVVSTHEQVLRTKN.

6. A composition of matter comprising one or more antibodies according to claim 4.

7. An antibody which specifically binds to a single type of keratin protein, said antibody being produced by immunization of an animal with a peptide of amino acid sequence that is the same as the carboxy-terminal 13 amino acids of said keratin, or a portion of that carboxy-terminal sequence, said amino acid sequence having been found to be unique to said keratin, said peptide having been covalently attached to a carrier protein prior to immunization of the animal.

8. A method for the identification of a normal cell type, or for the diagnosis of a diseased state of a cell type, based upon the types of keratin expressed in said cell, which comprises:
   1) contacting said cell with an antibody according to claim 4,
   2) determining the amount of specific binding of said antibody which occurs as a result of step (1).

9. The method according to claim 8, wherein the amount of specific binding is determined in step (2) by a method selected from the group consisting of:
   a) determining the activity of an enzyme bound to the cell through covalent linkage to a second antibody which specifically binds to the antibody used in step (1), and
   b) determining the activity of an enzyme covalently linked directly to the antibody used in step (1).

10. The method according to claim 8, wherein said cell is selected from the group of cell types consisting of: skin cells, lung cells, esophageal cells, colon epithelial cells, bladder cells, liver cells, vaginal cells, hair follicle cells, breast cells and neoplastic and preneoplastic variants of these cells types.

11. A method for the identification of a normal cell type, or for the diagnosis of a diseased state of a cell type, based upon the types of keratin expressed in said cell, which comprises:
   1) contacting said cell with an antibody according to claim 5,
   2) determining the amount of specific binding of said antibody which occurs as a result of step (1).

12. The method according to claim 11, wherein the amount of specific binding is determined in step (2) by a method selected from the group consisting of:
   a) determining the activity of an enzyme bound to the cell through covalent linkage to a second antibody which specifically binds to the antibody used in step (1), and
   b) determining the activity of an enzyme covalently linked directly to the antibody used in step (1).

13. The method according to claim 11, wherein said cell is selected from the group of cell types consisting of: skin cells, lung cells, esophageal cells, colon epithelial cells, bladder cells, liver cells, vaginal cells, hair follicle cells, breast cells and neoplastic and preneoplastic variants of these cell types.

* * * * *